United States Patent
Barth et al.

(10) Patent No.: US 7,741,363 B2
(45) Date of Patent: Jun. 22, 2010

(54) 3-ACYLINDOLE DERIVATIVES, PREPARATION AND THERAPEUTIC USE THEREOF

(75) Inventors: Francis Barth, Paris (FR); Claude Vernhet, Paris (FR); Murielle Rinaldi-Carmona, Paris (FR); CaroleElisabeth Guillaumont-Legeay, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/120,509

(22) Filed: May 14, 2008

(65) Prior Publication Data

US 2008/0275102 A1 Nov. 6, 2008

Related U.S. Application Data

(63) Continuation of application No. PCT/FR2006/002535, filed on Nov. 17, 2006.

(30) Foreign Application Priority Data

Nov. 18, 2005 (FR) .................... 05 11740

(51) Int. Cl.
A61K 31/405 (2006.01)
C07D 209/12 (2006.01)

(52) U.S. Cl. ...................... 514/419; 548/493
(58) Field of Classification Search .................. None
See application file for complete search history.

(56) References Cited

U.S. PATENT DOCUMENTS 5,532,237 A 7/1996 Gallant et al.
6,995,184 B2 * 2/2006 Barth et al. .................. 514/419

FOREIGN PATENT DOCUMENTS

WO WO 02/42269 5/2002
WO WO 03/097597 11/2003
WO WO 2006/069196 6/2006

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Vippagunta, Sudha R. "Crystalline Solids." Advanced Drug Delivery Reviews 48(2001): 3-26.*
Huffman, J. W., et. al., 1-Pentyl-3-Phenylacetylindoles, a new class of cannabimimetic indoles, Bioorganic & Medicinal Chemistry Letters, vol. 15, (2005) pp. 4110-4113.

* cited by examiner

Primary Examiner—Golam M. M. Shameem
Assistant Examiner—Alicia L Fierro
(74) Attorney, Agent, or Firm—Balaram Gupta

(57) ABSTRACT

The invention relates to compounds of formula (I), wherein X, $R_1$, $R_2$, $R_3$, $R_4$ and $R_5$ are as described herein.

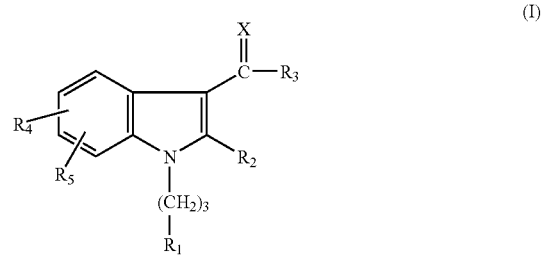

The invention also includes preparative methods for the preparation of compounds of formula (I). A method for the therapeutic use of the inventive compounds is also disclosed and claimed.

11 Claims, No Drawings

3-ACYLINDOLE DERIVATIVES, PREPARATION AND THERAPEUTIC USE THEREOF

This application is a continuation of International application No. PCT/FR2006/002,535, filed Nov. 17, 2006, which is incorporated herein by reference in its entirety; which claims the benefit of priority of French Patent Application No. 05/11,740, filed Nov. 18, 2005.

A subject-matter of the present invention is novel 3-acylindole derivatives having an affinity for cannabinoid $CB_2$ receptors, their preparation and their application in therapeutics.

$\Delta^9$-THC is the main active constituent extracted from *Cannabis sativa* [Paton, Annual Review in Pharmacology (1975), 15, 191-220].

Numerous papers have described not only psychotropic effects of cannabinoids but also an influence of the latter on the immune function [Klein et al., Immunology Today (1998), 19, 373-381], the control of pain [Pertwee, Progress in Neurobiology (2001), 63, 569-611], food intake [Cota et al., International Journal of Obesity (2003), 27, 289-301] and many other biological functions [Nahas et al., Marihuana and Medicine (1999), Humana Press, Totowa, N.J., USA].

The effects of cannabinoids are due to interaction with specific high affinity G protein-coupled receptors present at the central and peripheral level [Howlett et al., Pharmacological Reviews (2002), 54, 161-2002].

The central effects of cannabinoids concern a first type of cannabinoid receptor ($CB_1$) present mainly in the brain but also in the periphery [Matsuda et al., Nature (1990), 346, 561-564]. Furthermore, Munro et al. [Nature (1993), 365, 61-65] cloned a second type of cannabinoid receptor referred to as $CB_2$, which is present in the periphery and in particular in the cells of the immune system.

Some indole derivatives have been cited in the prior art as exhibiting an affinity for $CB_2$ receptors.

Thus, U.S. Pat. No. 5,532,237 discloses compounds of formula:

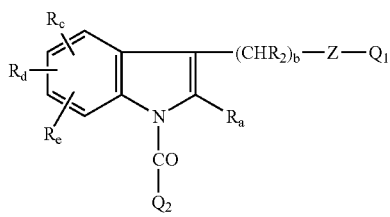

(A)

in which the substituents have different values.

Patent Application EP 833 818 discloses compounds of formula:

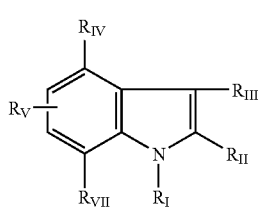

(B)

in which the substituents have different values.

Furthermore, U.S. Pat. No. 4,581,354 discloses active indole derivatives as analgesics and antiinflammatories of formula:

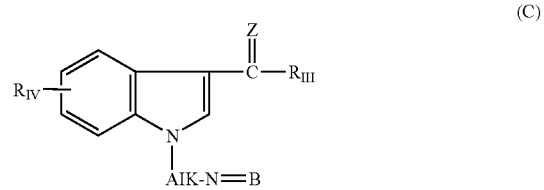

(C)

in which Z can represent oxygen or an NOH group.

International Patent Application WO 2002/42269 discloses aroylindole derivatives of formula:

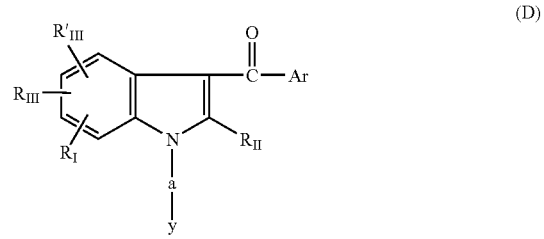

(D)

in which the substituents have different values.

International Patent Application WO 2003/097597 discloses compounds of formula:

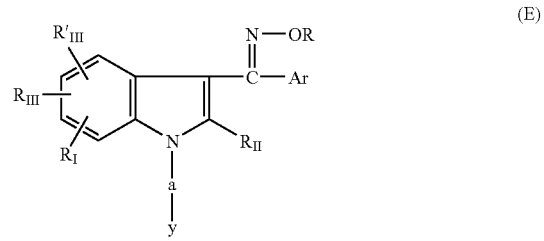

(E)

in which the substituents have different values.

International Patent Application WO 2006/069196 discloses compounds of

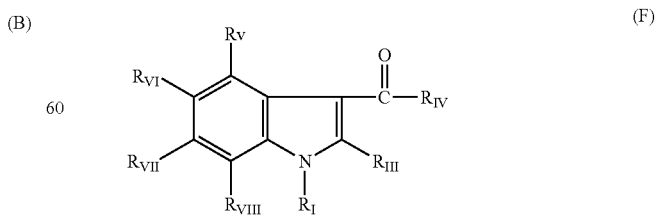

(F)

in which the substituents have different values.

A subject-matter of the present invention is compounds corresponding to the formula (I):

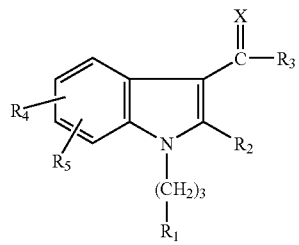

in which:
- X represents an oxygen atom or an =N—O—R$_6$ group;
- R$_1$ represents a group chosen from —N(R$_7$)SO$_2$R$_8$, —N(R$_7$)SO$_2$NR$_9$R$_{10}$, —SR$_8$, —SOR$_8$, —SO$_2$R$_8$ or —SO$_2$NR$_9$R$_{10}$;
- R$_2$ represents a hydrogen atom or a (C$_1$-C$_4$)alkyl;
- R$_3$ represents:
  - a (C$_1$-C$_6$)alkyl which is unsubstituted or substituted by:
    - a) one or more halogen atoms;
    - b) a nonaromatic C$_3$-C$_{12}$ carbocycle which is saturated or unsaturated and unsubstituted or substituted one or more times by a (C$_1$-C$_4$)alkyl;
    - c) a phenyl which is unsubstituted or substituted one or more times by substituents chosen independently from a halogen atom, an Alk group, an OAlk group, an —S(O)$_n$Alk group, a nitro or a cyano;
    - d) a naphthyl which is unsubstituted or substituted one or more times by substituents chosen independently from a halogen atom, a (C$_1$-C$_4$)alkyl, a (C$_1$-C$_4$)alkoxy or a trifluoromethyl radical;
  - a nonaromatic C$_3$-C$_{12}$ carbocycle which is saturated or unsaturated and which is substituted by a phenyl itself unsubstituted or substituted one or more times by substituents chosen independently from a halogen atom, a (C$_1$-C$_4$)alkyl, a (C$_1$-C$_4$)alkoxy or a trifluoromethyl radical;
  - a benzhydrylmethyl;
- R$_4$ and R$_5$ each independently represent a hydrogen atom, a halogen atom, a (C$_1$-C$_4$)alkyl, a (C$_1$-C$_4$)alkoxy, a trifluoromethyl radical or a nitro;
- R$_6$ represents a hydrogen atom or a (C$_1$-C$_4$)alkyl;
- R$_7$ represents a hydrogen atom or a (C$_1$-C$_4$)alkyl;
- R$_8$ represents a (C$_1$-C$_4$)alkyl or a trifluoromethyl radical;
- R$_9$ and R$_{10}$ each independently represent a hydrogen atom or a (C$_1$-C$_4$)alkyl;
- n represents 0, 1 or 2;
- Alk represents a (C$_1$-C$_4$)alkyl which is unsubstituted or substituted one or more times by a fluorine atom.

The compounds of formula (I) can comprise one or more asymmetric carbon atoms. They can thus exist in the form of enantiomers or of diastereoisomers. These enantiomers and diastereoisomers, and their mixtures, including racemic mixtures, form part of the invention.

The compounds of formula (I) in which X represents an =N—O—R$_6$ group are oximes or oxime ethers and can exist in two forms: Z and E. The present invention comprises each of the two isomers and a mixture of these two isomers in all proportions.

When the compounds of formula (I) comprise a sulfur atom, all the optical isomers and their mixture in any proportions are subject-matters of the invention.

The compounds of formula (I) can exist in the form of hydrates or of solvates, namely in the form of combinations or associations with one or more molecules of water or with a solvent. Such hydrates and solvates also form part of the invention.

The term "halogen atom" is understood to mean a bromine, chlorine, fluorine or iodine atom.

The term "(C$_1$-C$_4$)alkyl", or "(C$_1$-C$_6$)alkyl" respectively is understood to mean a linear or branched alkyl radical of one to four carbon atoms or of one to six carbon atoms respectively, such as the methyl, ethyl, propyl, isopropyl, butyl, isobutyl, sec-butyl, tert-butyl, pentyl, isopentyl, hexyl or isohexyl radical.

The term "(C$_1$-C$_4$)alkoxy" is understood to mean a linear of branched alkoxy radical of one to four carbon atoms, such as the methoxy, ethoxy, propoxy, isopropoxy, butoxy, sec-butoxy or tert-butoxy radical.

The nonaromatic C$_3$-C$_{12}$ carbocyclic radicals which are saturated or unsaturated comprise monocyclic or condensed, bridged or spiro polycyclic radicals. The monocyclic radicals include cycloalkyls, for example cyclopropyl, cyclobutyl, cyclopentyl, cyclohexyl, cycloheptyl or cyclooctyl, or cycloalkenyls, for example cyclohexenyl. The condensed, bridged or spiro di- or tricyclic radicals include, for example, the norbornyl, bornyl, isobornyl, noradamantyl, adamantyl, spiro[5.5]undecyl, bicyclo[2.2.1]heptyl, bicyclo[3.2.1]octyl or bicyclo[3.1.1]heptyl radicals.

The following are singled out among the compounds of formula (I) which are subject-matters of the invention:
- the compounds of formula (IA) in which X represents an oxygen atom and the R$_1$ to R$_5$ substituents are as defined for the compounds of formula (I);
- the compounds of formula (IB) in which X represents an =N—O—R$_6$ group and the R$_1$ to R$_6$ substituents are as defined for the compounds of formula (I);
- the compounds of formula (IC) in which X represents an oxygen atom and R$_3$ represents:
  - a (C$_1$-C$_6$)alkyl which is unsubstituted or substituted by:
    - a) one or more halogen atoms;
    - b) a nonaromatic C$_3$-C$_{12}$ carbocycle which is saturated or unsaturated and unsubstituted or substituted one or more times by a (C$_1$-C$_4$)alkyl;
    - c) a phenyl which is unsubstituted or substituted one or more times by substituents chosen independently from a halogen atom, an Alk group, an OAlk group, an —S(O)$_n$Alk group, a nitro or a cyano;
    - d) a naphthyl which is unsubstituted or substituted one or more times by substituents chosen independently from a halogen atom, a (C$_1$-C$_4$)alkyl, a (C$_1$-C$_4$)alkoxy or a trifluoromethyl radical;
  - a benzhydrylmethyl;

the R$_1$, R$_2$, R$_4$ and R$_5$ substituents being as defined for the compounds of formula (I);
- the compounds of formula (ID) in which X represents an oxygen atom and R$_3$ represents:
  - a nonaromatic C$_3$-C$_{12}$ carbocycle which is saturated or unsaturated and which is substituted by a phenyl itself unsubstituted or substituted one or more times by substituents chosen independently from a halogen atom, a (C$_1$-C$_4$)alkyl, a (C$_1$-C$_4$)alkoxy or a trifluoromethyl radical;

the R$_1$, R$_2$, R$_4$ and R$_5$ substituents being as defined for the compounds of formula (I);
- the compounds of formula (IE) in which X represents an =N—O—R$_6$ group and R$_3$ represents:
  - a (C$_1$-C$_6$)alkyl which is unsubstituted or substituted by:
    - a) one or more halogen atoms;

b) a nonaromatic $C_3$-$C_{12}$ carbocycle which is saturated or unsaturated and unsubstituted or substituted one or more times by a $(C_1$-$C_4)$alkyl;

c) a phenyl which is unsubstituted or substituted one or more times by substituents chosen independently from a halogen atom, an Alk group, an OAlk group, an —S(O)$_n$Alk group, a nitro or a cyano;

d) a naphthyl which is unsubstituted or substituted one or more times by substituents chosen independently from a halogen atom, a $(C_1$-$C_4)$alkyl, a $(C_1$-$C_4)$alkoxy or a trifluoromethyl radical;

a benzhydrylmethyl;

the $R_1$, $R_2$, $R_4$, $R_5$ and $R_6$ substituents being as defined for the compounds of formula (I);

the compounds of formula (IF) in which X represents an =N—O—$R_6$ group and $R_3$ represents:

a nonaromatic $C_3$-$C_{12}$ carbocycle which is saturated or unsaturated and which is substituted by a phenyl itself unsubstituted or substituted one or more times by substituents chosen independently from a halogen atom, a $(C_1$-$C_4)$alkyl, a $(C_1$-$C_4)$alkoxy or a trifluoromethyl radical;

the $R_1$, $R_2$, $R_4$, $R_5$ and $R_6$ substituents being as defined for the compounds of formula (I).

Among the compounds of formula (I) which are subject-matters of the invention, a first group of compounds is composed of the compounds for which:

X represents an oxygen atom or an =N—OH, =N—OCH$_3$ or =N—O—CH$_2$CH$_3$ group;

$R_1$ represents a group chosen from —NHSO$_2$CH$_3$, —NHSO$_2$CF$_3$, —NHSO$_2$N(CH$_3$)$_2$, —S—CH$_3$, —SO—CH$_3$ or —SO$_2$—CH$_3$;

$R_2$ represents a hydrogen atom, a methyl or an ethyl;

$R_3$ represents:

a tert-butyl, an isobutyl, a 2,2-dimethylpropyl, an adamantylmethyl, a phenylmethyl, a (2-bromophenyl)methyl, a (2-chlorophenyl)methyl, a (2-fluorophenyl)methyl, a (3-methoxyphenyl)methyl, a [2-(trifluoromethyl)phenyl]methyl, a [3-(trifluoromethyl)phenyl]methyl, a [4-(trifluoromethyl)phenyl]methyl, a (2,4-dichlorophenyl)methyl, a (2,3-difluorophenyl)methyl, a [2-fluoro-3-(trifluoromethyl)phenyl]methyl, a [2-fluoro-5-(trifluoromethyl)phenyl]methyl, a [3-fluoro-5-(trifluoromethyl)phenyl]methyl, a 1-methyl-1-phenylethyl, a 2-phenylethyl, a 2-(2-chlorophenyl)ethyl, a 3-phenylpropyl, a naphthylmethyl, a (2-methylphenyl)methyl, a (2-nitrophenyl)methyl, a [3-(trifluoromethylthio)phenyl]methyl, a (2-methoxyphenyl)methyl, a [2-(trifluoromethylthio)phenyl]methyl, a [2-(trifluoromethoxy)phenyl]methyl or a (2-cyanophenyl)methyl;

a 1-phenylcyclopropyl, a 2-phenylcyclopropyl, a 1-phenylcyclopentyl, a 1-(2-fluorophenyl)cyclopentyl or a 1-phenylcyclohexyl;

a benzhydrylmethyl;

$R_4$ represents a hydrogen atom or is in the 6-position of the indole and represents a chlorine atom or a methyl;

$R_5$ represents a hydrogen atom or is in the 7-position of the indole and represents a bromine, chlorine or fluorine atom, a methoxy or a nitro;

and their hydrates or their solvates.

Mention may be made, among the compounds of the latter group, of the compounds of formula (IA) for which:

X represents an oxygen atom;

$R_1$ represents a group chosen from —NHSO$_2$CH$_3$, —NHSO$_2$CF$_3$, —NHSO$_2$N(CH$_3$)$_2$, —S—CH$_3$, —SO—CH$_3$ or —SO$_2$—CH$_3$;

$R_2$ represents a hydrogen atom, a methyl or an ethyl;

$R_3$ represents:

a tert-butyl, an isobutyl, a 2,2-dimethylpropyl, an adamantylmethyl, a phenylmethyl, a (2-bromophenyl)methyl, a (2-chlorophenyl)methyl, a (2-fluorophenyl)methyl, a (3-methoxyphenyl)methyl, a [2-(trifluoromethyl)phenyl]methyl, a [3-(trifluoromethyl)phenyl]methyl, a [4-(trifluoromethyl)phenyl]methyl, a (2,4-dichlorophenyl)methyl, a (2,3-difluoro-phenyl)methyl, a [2-fluoro-3-(trifluoromethyl)phenyl]methyl, a [2-fluoro-5-(trifluoromethyl)phenyl]methyl, a [3-fluoro-5-(trifluoromethyl)phenyl]methyl, a 1-methyl-1-phenylethyl, a 2-phenylethyl, a 2-(2-chlorophenyl)ethyl, a 3-phenylpropyl, a naphthylmethyl, a (2-methylphenyl)methyl, a (2-nitrophenyl)methyl, a [3-(trifluoromethylthio)phenyl]methyl, a (2-methoxyphenyl)methyl, a [2-(trifluoromethylthio)phenyl]methyl, a [2-(trifluoromethoxy)phenyl]methyl or a (2-cyanophenyl)methyl;

a 1-phenylcyclopropyl, a 2-phenylcyclopropyl, a 1-phenylcyclopentyl, a 1-(2-fluorophenyl)cyclopentyl or a 1-phenylcyclohexyl;

a benzhydrylmethyl;

$R_4$ represents a hydrogen atom or is in the 6-position of the indole and represents a chlorine atom or a methyl;

$R_5$ represents a hydrogen or is in the 7-position of the indole and represents a bromine, chlorine or fluorine atom, a methoxy or a nitro;

and their hydrates or their solvates.

Mention may also be made of the compounds of formula (IB) for which:

X represents an =N—OH, =N—OCH$_3$ or =N—O—CH$_2$CH$_3$ group;

$R_1$ represents a group chosen from —NHSO$_2$CH$_3$, —S—CH$_3$ or —SO$_2$—CH$_3$;

$R_2$ represents a hydrogen atom or a methyl;

$R_3$ represents:

a (2-bromophenyl)methyl, a (2-chlorophenyl)methyl or a 2-(2-chlorophenyl)ethyl;

a 1-phenylcyclopentyl;

$R_4$ represents a hydrogen atom or is in the 6-position of the indole and represents a chlorine atom;

$R_5$ is in the 7-position of the indole and represents a chlorine atom; and their hydrates or their solvates.

Mention may also be made of the compounds of formula (IC) for which:

X represents an oxygen atom;

$R_1$ represents a group chosen from —NHSO$_2$CH$_3$, —NHSO$_2$CF$_3$, —NHSO$_2$N(CH$_3$)$_2$, —S—CH$_3$, —SO—CH$_3$ or —SO$_2$—CH$_3$;

$R_2$ represents a hydrogen atom, a methyl or an ethyl;

$R_3$ represents:

a tert-butyl, an isobutyl, a 2,2-dimethylpropyl, an adamantylmethyl, a phenylmethyl, a (2-bromophenyl)methyl, a (2-chlorophenyl)methyl, a (2-fluorophenyl)methyl, a (3-methoxyphenyl)methyl, a [2-(trifluoromethyl)phenyl]methyl, a [3-(trifluoromethyl)phenyl]methyl, a [4-(trifluoromethyl)phenyl]methyl, a (2,4- dichlorophenyl)methyl, a (2,3-difluorophenyl) methyl, a [2-fluoro-3-(trifluoromethyl)phenyl] methyl, a [2-fluoro-5-(trifluoromethyl)phenyl] methyl, a [3-fluoro-5-(trifluoromethyl)phenyl] methyl, a 1-methyl-1-phenylethyl, a 2-phenylethyl, a 2-(2-chlorophenyl)ethyl, a 3-phenylpropyl, a naphthylmethyl, a (2-methylphenyl)methyl, a (2-nitrophenyl)methyl, a [3-(trifluoromethylthio)phenyl]methyl, a (2-methoxyphenyl)methyl, a [2-(trifluoromethylthio)phenyl]methyl, a [2-(trifluoromethoxy)phenyl]methyl or a (2-cyanophenyl)methyl;
a benzhydrylmethyl;
$R_4$ represents a hydrogen atom or is in the 6-position of the indole and represents a chlorine atom or a methyl;
$R_5$ represents a hydrogen or is in the 7-position of the indole and represents a bromine, chlorine or fluorine atom, a methoxy or a nitro;

and their hydrates or their solvates.

Mention may also be made of the compounds of formula (ID) for which:
X represents an oxygen atom;
$R_1$ represents a group chosen from —NHSO$_2$CH$_3$ or —NHSO$_2$N(CH$_3$)$_2$;
$R_2$ represents a methyl;
$R_3$ represents:
a 1-phenylcyclopropyl, a 2-phenylcyclopropyl, a 1-phenylcyclopentyl, a 1-(2-fluorophenyl)cyclopentyl or a 1-phenylcyclohexyl;
$R_4$ represents a hydrogen atom or is in the 6-position of the indole and represents a chlorine atom;
$R_5$ represents a hydrogen atom or is in the 7-position of the indole and represents a bromine or chlorine atom;
and their hydrates or their solvates.

Mention may also be made of the compounds of formula (IE) for which:
X represents an =N—OH, =N—OCH$_3$ or =N—O—CH$_2$CH$_3$ group;
$R_1$ represents a group chosen from —NHSO$_2$CH$_3$, —S—CH$_3$ or —SO$_2$—CH$_3$;
$R_2$ represents a hydrogen atom or a methyl;
$R_3$ represents:
a (2-bromophenyl)methyl, a (2-chlorophenyl)methyl or a 2-(2-chlorophenyl)ethyl;
$R_4$ represents a hydrogen atom or is in the 6-position of the indole and represents a chlorine atom;
$R_5$ is in the 7-position of the indole and represents a chlorine atom;
and their hydrates or their solvates.

Mention may also be made of the compounds of formula (IF) for which:
X represents an =N—OCH$_3$ group;
$R_1$ represents a group chosen from —NHSO$_2$CH$_3$;
$R_2$ represents a methyl;
$R_3$ represents a 1-phenylcyclopentyl;
$R_4$ represents a hydrogen atom;
$R_5$ is in the 7-position of the indole and represents a chlorine atom;
and their hydrates or their solvates.

Mention may in particular be made, among the compounds of formula (I) which are subject-matters of the invention, of the following compounds:
N-[3-[7-bromo-3-(3,3-dimethylbutanoyl)-2-methyl-1H-indol-1-yl]propyl]methanesulfonamide;
N-[3-[7-bromo-2-methyl-3-[[2-(trifluoromethyl)phenyl] acetyl]-1H-indol-1-yl]propyl]methanesulfonamide;
N-[3-[7-bromo-3-[[1-(2-fluorophenyl)cyclopentyl]carbonyl]-2-methyl-1H-indol-1-yl]propyl]methanesulfonamide;
N-[3-[7-chloro-3-(3,3-dimethylbutanoyl)-2-methyl-1H-indol-1-yl]propyl]methanesulfonamide;
N-[3-[3-(1-adamantylacetyl)-7-chloro-2-methyl-1H-indol-1-yl]propyl]methanesulfonamide;
N-[3-[3-[(2-bromophenyl)acetyl]-7-chloro-2-methyl-1H-indol-1-yl]propyl]methanesulfonamide;
N-[3-[7-chloro-3-[(2-chlorophenyl)acetyl]-2-methyl-1H-indol-1-yl]propyl]methanesulfonamide;
N-[3-[7-chloro-2-methyl-3-[[2-(trifluoromethyl)phenyl] acetyl]-1H-indol-1-yl]propyl]methanesulfonamide;
N-[3-[7-chloro-3-[(2,3-difluorophenyl)acetyl]-2-methyl-1H-indol-1-yl]propyl]methanesulfonamide;
N-[3-[7-chloro-2-methyl-3-[(1-phenylcyclopropyl)carbonyl]-1H-indol-1-yl]propyl]methanesulfonamide;
N-[3-[7-chloro-2-methyl-3-[(1-phenylcyclopentyl)carbonyl]-1H-indol-1-yl]propyl]methanesulfonamide;
N-[3-[7-chloro-3-[[1-(2-fluorophenyl)cyclopentyl]carbonyl]-2-methyl-1H-indol-1-yl]propyl]methanesulfonamide;
N-[3-[7-chloro-2-methyl-3-[(1-phenylcyclohexyl)carbonyl]-1H-indol-1-yl]propyl]methanesulfonamide;
N-[3-[7-fluoro-2-methyl-3-[[2-(trifluoromethyl)phenyl] acetyl]-1H-indol-1-yl]propyl]methanesulfonamide;
N-[3-[7-bromo-3-(3,3-dimethylbutanoyl)-2,6-dimethyl-1H-indol-1-yl]propyl]methanesulfonamide;
N-[3-[7-bromo-3-[(2-chlorophenyl)acetyl]-2,6-dimethyl-1H-indol-1-yl]propyl]methanesulfonamide;
1-[7-chloro-2-methyl-1-[3-(methylthio)propyl]-1H-indol-3-yl)-2-[2-(trifluoromethyl)phenyl]ethanone;
2-(2-bromophenyl)-1-[6,7-dichloro-2-methyl-1-[3-(methylthio)propyl]-1H-indol-3-yl]ethanone oxime;
2-(1-adamantyl)-1-[6,7-dichloro-2-methyl-1-[3-(methylthio)propyl]-1H-indol-3-yl]ethanone;
2-(1-adamantyl)-1-[6,7-dichloro-2-methyl-1-[3-(methylsulfinyl)propyl]-1H-indol-3-yl]ethanone;
N-[3-[7-bromo-3-[(2-chlorophenyl)acetyl]-2-methyl-1H-indol-1-yl]propyl]methanesulfonamide;
N-[3-[7-bromo-3-[(2-fluorophenyl)acetyl]-2-methyl-1H-indol-1-yl]propyl]methanesulfonamide;
N-[3-[7-bromo-2-methyl-3-[(2-methylphenyl)acetyl]-1H-indol-1-yl]propyl]methanesulfonamide;
N-[3-[7-bromo-2-methyl-3-[(2-nitrophenyl)acetyl]-1H-indol-1-yl]propyl]methanesulfonamide;
N-[3-[7-chloro-2-methyl-3-[(2-methylphenyl)acetyl]-1H-indol-1-yl]propyl]methanesulfonamide;
N-[3-[7-chloro-3-[(2-methoxyphenyl)acetyl]-2-methyl-1H-indol-1-yl]propyl]methanesulfonamide;
N-[3-[7-chloro-2-methyl-3-[[2-[(trifluoromethyl)thio] phenyl]acetyl]-1H-indol-1-yl]propyl]methanesulfonamide;
N-[3-[3-[(2-bromophenyl)acetyl]-7-fluoro-2-methyl-1H-indol-1-yl]propyl]methanesulfonamide;
N-[3-[3-[(2-chlorophenyl)acetyl]-7-fluoro-2-methyl-1H-indol-1-yl]propyl]methanesulfonamide;
N-[3-[7-fluoro-3-[(2-fluorophenyl)acetyl]-2-methyl-1H-indol-1-yl]propyl]methanesulfonamide;
N-[3-[7-fluoro-2-methyl-3-[(2-methylphenyl)acetyl]-1H-indol-1-yl]propyl]methanesulfonamide;
N-[3-[7-fluoro-3-[(2-methoxyphenyl)acetyl]-2-methyl-1H-indol-1-yl]propyl]methanesulfonamide;
N-[3-[7-bromo-2,6-dimethyl-3-[[2-(trifluoromethyl)phenyl]acetyl]-1H-indol-1-yl]propyl]methanesulfonamide;

N-[3-[3-[(2-bromophenyl)acetyl]-7-methoxy-2-methyl-1H-indol-1-yl]propyl]methanesulfonamide;
N-[3-[7-methoxy-2-methyl-3-[[2-(trifluoromethyl)phenyl]acetyl]-1H-indol-1-yl]propyl]methanesulfonamide;
N-[3-[3-[(2-chlorophenyl)acetyl]-7-nitro-1H-indol-1-yl]propyl]methanesulfonamide;
N-[3-[3-[(2-fluorophenyl)acetyl]-7-nitro-1H-indol-1-yl]propyl]methanesulfonamide;
N-[3-[3-[(2-methylphenyl)acetyl]-7-nitro-1H-indol-1-yl]propyl]methanesulfonamide;
N-[3-[7-nitro-3-[[2-(trifluoromethyl)phenyl]acetyl]-1H-indol-1-yl]propyl]methanesulfonamide;
N-[3-[3-[(2-bromophenyl)acetyl]-7-nitro-1H-indol-1-yl]propyl]methanesulfonamide;
N-[3-[3-[(2-methoxyphenyl)acetyl]-7-nitro-1H-indol-1-yl]propyl]methanesulfonamide;
N-[3-[7-nitro-3-[[(2-(trifluoromethoxy)phenyl]acetyl]-1H-indol-1-yl]propyl]methanesulfonamide;
N-[3-[7-nitro-3-[(2-nitrophenyl)acetyl]-1H-indol-1-yl]propyl]methanesulfonamide;
N-[3-[7-bromo-3-[(2-bromophenyl)acetyl]-2-methyl-1H-indol-1-yl]propyl]methanesulfonamide;
N-[3-[7-bromo-3-[(2-methoxyphenyl)acetyl]-2-methyl-1H-indol-1-yl]propyl]methanesulfonamide;
N-[3-[7-bromo-2-methyl-3-[[2-(trifluoromethoxy)phenyl]acetyl]-1H-indol-1-yl]propyl]methanesulfonamide;
N-[3-[7-fluoro-2-methyl-3-[[2-(trifluoromethoxy)phenyl]acetyl]-1H-indol-1-yl]propyl]methanesulfonamide;
N-[3-[7-fluoro-2-methyl-3-[(2-nitrophenyl)acetyl]-1H-indol-1-yl]propyl]methanesulfonamide;
1,1,1-trifluoro-N-[3-[7-fluoro-2-methyl-3-[[2-(trifluoromethyl)phenyl]acetyl]-1H-indol-1-yl]propyl]methanesulfonamide;

and their hydrates or their solvates.

In accordance with the invention, the compounds of formula (I) in which X represents an oxygen atom can be prepared according to a process which is characterized in that:
a compound of formula:

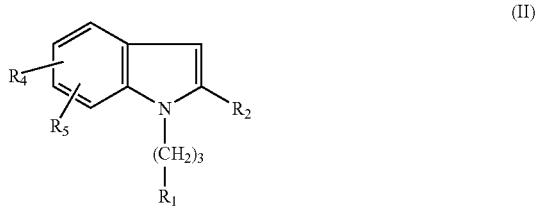

(II)

in which $R_1$, $R_2$, $R_4$ and $R_5$ are as defined for a compound of formula (I), is reacted, in the presence of a Lewis acid, with an acid halide of formula:

(III)

in which $R_3$ is as defined for a compound of formula (I) and Hal represents a halogen atom.

The reaction is carried out under Friedel and Crafts conditions in the presence of a Lewis acid, such as aluminum chloride or ethylaluminum dichloride, in a solvent, such as dichloromethane or toluene, at a temperature of between −30° C. and ambient temperature, according to the process described in J. Med. Chem., 1995, 38, 3094.

In accordance with the invention, the compounds of formula (I) in which X represents an =N—O—$R_6$ group can be prepared according to a process which is characterized in that:
a compound of formula:

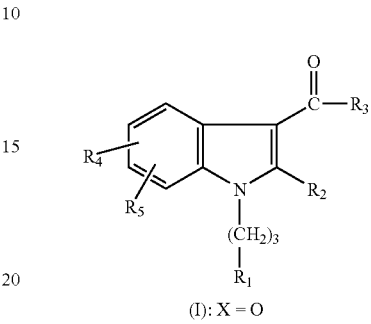

(I): X = O in which $R_1$, $R_2$, $R_3$, $R_4$ and $R_5$ are as defined for a compound of formula (I), is reacted, in the presence of a base, with a hydroxylamine derivative of formula:

$H_2N—O—R_6$ (IV)

in which $R_6$ is as defined for a compound of formula (I).

The reaction is carried out in the presence of a base, such as pyridine, in a solvent, such as ethanol, at a temperature between ambient temperature and the reflux temperature of the solvent. The compound obtained is generally composed of a mixture of the Z and E isomers of the oxime or of the oxime ether. The Z and E isomers can be separated using processes known to a person skilled in the art, for example by preparative chromatography.

According to an alternative form of this process, a compound of formula (I) in which X=N—$OR_6$ in which $R_6$=($C_1$-$C_4$)alkyl can also be prepared by reaction of a compound of formula (I) in which $R_6$=H with a ($C_1$-$C_4$)alkyl halide or with a ($C_1$-$C_4$)alkyl sulfate. The reaction is carried out in the presence of a base, such as sodium hydroxide, in a solvent, such as ethanol, or in the presence of sodium hydride in a solvent, such as tetrahydrofuran, at a temperature between ambient temperature and the reflux temperature of the solvent.

According to another alternative form of the above processes, a compound of formula (I) in which $R_1$=—$SOR_8$ or —$SO_2R_8$ can be prepared by reaction of a compound of formula (I) in which $R_1$=—$SR_8$ with an oxidizing agent. Use may be made, as oxidizing agent, of aqueous hydrogen peroxide solution or 3-chloroperbenzoic acid in a solvent, such as dichloromethane, and at a temperature between 0° C. and ambient temperature.

Depending on the number of equivalents of oxidizing agent used and depending on the reaction temperature, a sulfoxide ($R_1$=—$SOR_8$) or a sulfone ($R_1$=—$SO_2R_8$) is obtained. It is also possible to obtain a mixture of the two compounds which is separated by using processes known to a person skilled in the art, for example by preparative chromatography.

The compounds of formula (I) thus obtained can be subsequently separated from the reaction medium and purified according to conventional methods, for example by crystallization or chromatography.

The compounds of formula (II) are known and are prepared according to known methods, such as those disclosed in WO 02/42269 or in WO 03/097597.

The compounds of formulae (III) and (IV) are known, are commercially available or are prepared according to known methods.

The following EXAMPLES describe the preparation of some compounds in accordance with the invention. These examples are not limiting and serve only to illustrate the present invention. The numbers of the compounds in the examples refer to those given in TABLE I below, in which the chemical structures and the physical properties of a few compounds according to the invention are illustrated.

The following abbreviations are used in the Preparations and in the Examples:
ether: diethyl ether
iso ether: diisopropyl ether
DMSO: dimethyl sulfoxide
DMF: N,N-dimethylformamide
THF: tetrahydrofuran
MeOH: methanol
DCM: dichloromethane
EtOAc: ethyl acetate
DIPEA: diisopropylethylamine
TFA: trifluoroacetic acid
M.p.: melting point
AT: ambient temperature
HPLC: high performance liquid chromatography The proton nuclear magnetic resonance ($^1$H NMR) spectra are recorded at 200 MHz in $d_6$-DMSO. The chemical shifts δ are expressed in parts per million (ppm). Use is made of the following abbreviations in interpreting the spectra: s: singlet, d: doublet, t: triplet, q: quartet, m: unresolved peak, mt: multiplet, bs: broad singlet, sd: split doublet.

The compounds according to the invention are analyzed by LC/UV/MS (liquid chromatography/UV detection/mass spectrometry) coupling. The molecular peak (MH$^+$) and the retention time (rt) in minutes are measured. The conditions used are as follows:

Use is made of a Symmetry $C_{18}$ column of 2.1×50 mm, 3.5 μm, at 30° C., flow rate 0.4 ml/minute.

The eluent is composed as follows:
Solvent A: 0.005% of trifluoroacetic acid in water at pH=3.15;
Solvent B: 0.005% of trifluoroacetic acid in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Detection is carried out at λ=210 nm and the mass spectra are recorded in positive electrospray (ESI) mode in order to observe the ions resulting from the protonation of the compounds analyzed (MH$^+$).

Preparations
1. Preparations of the Compounds of Formula (II)
Preparation 1.1

N-[3-(2-Methyl-1H-indol-1-yl)propyl]methanesulfonamide (II): $R_1$=—NHSO$_2$CH$_3$; $R_2$=—CH$_3$; $R_4$=H; $R_5$=H.
This compound, described in TABLE 3 in Preparation 3.22 in WO 02/42269, is prepared according to the methods cited.

Preparation 1.2

N-[3-(7-Bromo-2-methyl-1H-indol-1-yl)propyl]methanesulfonamide (II): $R_1$=—NHSO$_2$CH$_3$; $R_2$=—CH$_3$; $R_4$=H; $R_5$=7-Br.
This compound, described in TABLE 3 in Preparation 3.5 in WO 02/42269, is prepared according to the methods cited.

Preparation 1.3

N-[3-(7-Chloro-2-methyl-1H-indol-1-yl)propyl]methanesulfonamide (II): $R_1$=—NHSO$_2$CH$_3$; $R_2$=—CH$_3$; $R_4$=H; $R_5$=7-Cl.
This compound is prepared according to the procedure described in stage B of Example 3 in WO 02/42269.

Preparation 1.4

N-[3-(7-Chloro-2-ethyl-1H-indol-1-yl)propyl]methanesulfonamide (II): $R_1$=—NHSO$_2$CH$_3$; $R_2$=—CH$_2$CH$_3$; $R_4$=H; $R_5$=7-Cl.
This compound, described in TABLE 3 in Preparation 3.9 in WO 02/42269, is prepared according to the methods cited.

Preparation 1.5

N-[3-(7-Fluoro-2-methyl-1H-indol-1-yl)propyl]methanesulfonamide (II): $R_1$=—NHSO$_2$CH$_3$; $R_2$=—CH$_3$; $R_4$=H; $R_5$=7-F.

A) 7-Fluoro-2-methyl-1H-indole 1600 ml of a 0.5M solution of isopropenylmagnesium bromide in THF are cooled to −25° C. under an argon atmosphere, a solution of 37.65 g of 2-fluoronitrobenzene in 250 ml of THF is then added dropwise and the mixture is left stirring at −20° C. for 1 hour. The reaction mixture is poured into a saturated NH$_4$Cl solution, the aqueous phase is extracted with ether and the combined organic phases are concentrated under vacuum. The residue is taken up in water and extracted with DCM, the organic phase is washed with water and with a saturated NaCl solution and dried over MgSO$_4$, and the solvent is evaporated under vacuum. The residue is chromatographed on silica gel, elution being carried out with a cyclohexane/EtOAc mixture (95/5; v/v). 12.35 g of the expected compound are obtained.

B) 1-(3-Chloropropyl)-7-fluoro-2-methyl-1H-indole

A solution of 10.4 g of the compound obtained in the preceding stage in 170 ml of toluene and then 1.04 g of tetrabutylammonium hydrogensulfate are added to a mixture of 15.64 g of crushed KOH in 300 ml of toluene and the mixture is heated at reflux for 30 minutes. 27.6 ml of 1-bromo-3-chloropropane are subsequently added and reflux is continued for 3 hours. The reaction mixture is poured into water, the organic phase is washed with water and with a saturated NaCl solution and dried over Na$_2$SO$_4$, and the solvent is evaporated under vacuum. 16.5 g of the expected compound are obtained.

C) 7-Fluoro-1-(3-iodopropyl)-2-methyl-1H-indole 76.9 g of NaI are added to a solution of 16.5 g of the compound obtained in the preceding stage in 900 ml of acetonitrile and the mixture is heated at reflux for 3 days. It is concentrated under vacuum, the residue is taken up in water and extracted with toluene, the organic phase is washed with water and with a saturated NaCl solution and dried over MgSO$_4$, and the solvent is evaporated under vacuum. 20.8 g of the expected compound are obtained.

D) N-[3-(7-Fluoro-2-methyl-1H-indol-1-yl)propyl]methanesulfonamide 3.53 g of 60% sodium hydride in oil are introduced into 250 ml of DMF under a nitrogen atmosphere, the mixture is cooled to 5° C., a solution of 8.4 g of methane-sulfonamide in 125 ml of DMF is then added and the mixture is left stirring at 5° C. for 10 minutes. A solution of 7 g of the compound obtained in the preceding stage in 125 ml of DMF is subsequently added and the mixture is left stirring for 4 hours while allowing the temperature to return to AT. The reaction mixture is poured into water and extracted with DCM, the organic phase is washed with water and with a saturated NaCl solution and dried over MgSO$_4$, and the solvent is evaporated under vacuum. The residue is chromatographed on silica gel, elution being carried out with a cyclohexane/EtOAc mixture (60/40; v/v). 4.4 g of the expected compound are obtained.

Preparation 1.6

N-[3-(7-Bromo-2,6-dimethyl-1H-indol-1-yl)propyl]methanesulfonamide (II): $R_1$=—NHSO$_2$CH$_3$; $R_2$=—CH$_3$; $R_4$=6-CH$_3$; $R_5$=7-Br.

This compound, described in TABLE 3 in Preparation 3.24 in WO 02/42269, is prepared according to the methods cited.

Preparation 1.7

N-[3-(6,7-Dichloro-1H-indol-1-yl)propyl]methanesulfonamide (II): $R_1$=—NHSO$_2$CH$_3$; $R_2$=H; $R_4$=6-Cl; $R_5$=7-Cl.

A) 6,7-Dichloro-1H-indole 800 ml of a 1M solution of vinylmagnesium bromide in THF are cooled to −45° C. under a nitrogen atmosphere, a solution of 51.2 g of 2,3-dichloronitrobenzene in 1000 ml of THF is then added dropwise and the mixture is left stirring at −30° C. for 1 hour. The reaction mixture is poured onto 1000 ml of a saturated NH$_4$Cl solution and extracted with ether, the combined organic phases are washed with water and with a saturated NaCl solution and dried over MgSO$_4$, and the solvents are evaporated under vacuum. The residue is chromatographed on silica gel, elution being carried out with a cyclohexane/EtOAc mixture (95/5; v/v). 27.75 g of the expected compound are obtained.

B) 6,7-Dichloro-1-(3-chloropropyl)-1H-indole

A solution of 27.75 g of the compound obtained in the preceding stage in 600 ml of toluene and then 2.8 g of tetrabutylammonium hydrogensulfate are added to a mixture of 33.5 g of crushed KOH in 600 ml of toluene and the mixture is heated at reflux for 30 minutes. 50 ml of 1-bromo-3-chloropropane are subsequently added and reflux is continued for 2 hours. After cooling to AT, the reaction mixture is poured into water, the organic phase is washed with water and with a saturated NaCl solution and dried over MgSO$_4$, and the solvent is evaporated under vacuum. 39.2 g of the expected compound are obtained.

C) 6,7-Dichloro-1-(3-iodopropyl)-1H-indole 156.6 g of NaI are added to a solution of 39.2 g of the compound obtained in the preceding stage in 1200 ml of acetonitrile and the mixture is heated at reflux for 3 days. It is concentrated under vacuum, the residue is taken up in water and extracted with toluene, the organic phase is washed with water and with a saturated NaCl solution and dried over MgSO$_4$, and the solvent is evaporated under vacuum. 46.85 g of the expected compound are obtained.

D) N-[3-(6,7-Dichloro-1H-indol-1-yl)propyl]methanesulfonamide

A mixture of 4.5 g of 60% sodium hydride in oil in 250 ml of DMF is cooled to 5° C., a solution of 10.7 g of methanesulfonamide in 120 ml of DMF is added dropwise and the mixture is left stirring at 5° C. for 10 minutes. A solution of 10 g of the compound obtained in the preceding stage in 120 ml of DMF is subsequently added and the mixture is left stirring for 4 hours while allowing the temperature to return to AT. The reaction mixture is poured into water and extracted with DCM, the organic phase is washed with a saturated NaCl solution and dried over MgSO$_4$, and the solvent is evaporated under vacuum. The residue is chromatographed on silica gel, elution being carried out with a cyclohexane/EtOAc mixture (50/50; v/v). 5 g of the expected compound are obtained.

Preparation 1.8

N-[3-(6,7-Dichloro-2-methyl-1H-indol-1-yl)propyl]methanesulfonamide (II): $R_1$=—NHSO$_2$CH$_3$; $R_2$=—CH$_3$; $R_4$=6-Cl; $R_5$=7-Cl This compound is prepared according to the process described in stage C of Example 72 in WO 02/42269.

Preparation 1.9

N-[3-(5,7-Dichloro-2-methyl-1H-indol-1-yl)propyl]methanesulfonamide (II): $R_1$=—NHSO$_2$CH$_3$; $R_2$=—CH$_3$; $R_4$=5-Cl; $R_5$=7-Cl This compound is prepared according to the processes described in stages A, B, C and D of Preparation 1.7.

Preparation 1.10

N-[3-(7-Chloro-2-methyl-1H-indol-1-yl)propyl]-1,1,1-trifluoromethanesulphonamide (II): $R_1$=—NHSO$_2$CF$_3$; $R_2$=—CH$_3$; $R_4$=H; $R_5$=7-Cl This compound, described in TABLE 3 in Preparation 3.19 in WO 02/42269, is prepared according to the methods cited.

Preparation 1.11

N'-[3-(6,7-Dichloro-2-methyl-1H-indol-1-yl)propyl]-N,N-dimethylsulfamide (II): $R_1$=—NHSO$_2$N(CH$_3$)$_2$; $R_2$=—CH$_3$; $R_4$=6-Cl; $R_5$=7-Cl A) 6,7-Dichloro-1-(3-iodopropyl)-2-methyl-1H-indole This compound is prepared according to the procedure described in stage B of Example 72 in WO 02/42269.

B) N'-[3-(6,7-Dichloro-2-methyl-1H-indol-1-yl)propyl]-N,N-dimethylsulfamide

A mixture of 2.8 g of 60% sodium hydride in oil in 200 ml of DMF is cooled to 5° C., a solution of 8.68 g of N,N-dimethylsulfamide in 100 ml of DMF is added dropwise and the mixture is left stirring at 5° C. for 10 minutes. A solution of 6.45 g of the compound from the preceding stage in 100 ml of DMF is subsequently added and the mixture is left stirring for 4 hours while allowing the temperature to return to AT. The reaction mixture is poured into water and extracted with DCM, the organic phase is washed with water and with a saturated NaCl solution and dried over MgSO$_4$, and the solvent is evaporated under vacuum. The residue is chromatographed on silica gel, elution being carried out with a cyclohexane/EtOAc mixture (70/30; v/v). 4.05 g of the expected compound are obtained.

Preparation 1.12

7-Chloro-2-methyl-1-[3-(methylthio)propyl]-1H-indole (II): $R_1$=—S—CH$_3$; $R_2$=—CH$_3$; $R_4$=H; $R_5$=7-Cl This compound is prepared according to the procedure described in stage B of Example 1 in WO 02/42269.

Preparation 1.13

6,7-Dichloro-1-[3-(methylthio)propyl]-1H-indole (II): $R_1$=—S—CH$_3$; $R_2$=H; $R_4$=6-Cl; $R_5$=7-Cl 18.5 g of sodium methanethiolate are added to a solution of 46.8 g of the compound obtained in stage C of Preparation 1.7 in 700 ml of ethanol and the mixture is heated at reflux overnight. The reaction mixture is poured into a 10% NaOH solution and extracted with ether, the organic phase is washed with a 10% NaOH solution, with water and with a saturated NaCl solution and dried over MgSO$_4$, and the solvent is evaporated under vacuum. The residue is chromatographed on silica gel, elution being carried out with a cyclohexane/EtOAc mixture (95/5; v/v). 28.3 g of the expected compound are obtained.

Preparation 1.14

6,7-Dichloro-2-methyl-1-[3-(methylthio)propyl]-1H-indole (II): $R_1$=—S—CH$_3$; $R_2$=—CH$_3$; $R_4$=6-Cl; $R_5$=7-Cl

A) 6,7-Dichloro-1-(3-iodopropyl)-2-methyl-1H-indole

This compound is prepared according to the procedure described in stage B of Example 72 in WO 02/42269.

B) 6,7-Dichloro-2-methyl-1-[3-(methylthio)propyl]-1H-indole

A mixture of 12.6 g of the compound obtained in the preceding stage and 4.79 g of sodium methanethiolate in 250 ml of ethanol is heated at reflux for 24 hours. The reaction mixture is poured into a 10% NaOH solution and extracted with ether, the organic phase is washed with water and with a saturated NaCl solution and dried over MgSO$_4$, and the solvent is evaporated under vacuum. The residue is chromatographed on silica gel, elution being carried out with cyclohexane. 3.1 g of the expected compound are obtained.

Preparation 1.15

N-[3-(7-Methoxy-2-methyl-1H-indol-1-yl)propyl]methanesulfonamide (II): $R_1$=—NHSO$_2$CH$_3$; $R_2$=—CH$_3$; $R_4$=H; $R_5$=7-OCH$_3$

A) 7-Methoxy-2-methyl-1H-indole 800 ml of a 0.5M solution of isopropenylmagnesium bromide in THF is cooled to −40° C. under a nitrogen atmosphere, a solution of 20.4 g of 2-methoxynitrobenzene in 125 ml of THF is then added dropwise and the mixture is left stirring for 1 hour while allowing the temperature to return to 0° C. The reaction mixture is poured into a saturated NH$_4$Cl solution and extracted with ether, the organic phase is washed with a saturated NaCl solution and dried over MgSO$_4$, and the solvent is evaporated under vacuum. The residue is chromatographed on silica gel, elution being carried out with cyclohexane and then with a cyclohexane/EtOAc mixture (90/10; v/v). 2.45 g of the expected compound are obtained in the form of an oil.

B) 1-(3-Chloropropyl)-7-methoxy-2-methyl-1H-indole 3.41 g of crushed KOH and 0.245 g of tetrabutylammonium hydrogensulfate are added to a solution of 2.45 g of the compound from the preceding stage in 100 ml of toluene and then the mixture is heated at reflux for 20 minutes. 6 ml of 1-bromo-3-chloropropane are subsequently added and reflux is continued for 1 hour. After cooling to AT, the reaction mixture is poured into water and extracted with toluene, the organic phase is washed with a saturated NaCl solution and dried over MgSO$_4$, and the solvent is evaporated under vacuum. 5.15 g of the expected compound are obtained in the form of an oil.

C) 1-(3-Iodopropyl)-7-methoxy-2-methyl-1H-indole 22.3 g of NaI are added to a solution of 5.05 g of the compound from the preceding stage in 140 ml of acetonitrile and the mixture is heated at reflux overnight. The reaction mixture is concentrated under vacuum, the residue is taken up in water and extracted with toluene, the organic phase is washed with a saturated NaCl solution and dried over MgSO$_4$, and the solvent is evaporated under vacuum. 6.3 g of the expected compound are obtained.

D) N-[3-(7-Methoxy-2-methyl-1H-indol-1-yl)propyl]methanesulfonamide

A mixture of 3.04 g of 60% sodium hydride in oil in 200 ml of DMF is cooled to 5° C., a solution of 7.2 g of methanesulfonamide in 90 ml of DMF is added and the mixture is left stirring at 5° C. for 5 minutes. A solution of 6.25 g of the compound from the preceding stage in 90 ml of DMF is subsequently added and the mixture is left stirring overnight while allowing the temperature to return to AT. The reaction mixture is poured into water and extracted with DCM, the organic phase is washed with a saturated NaCl solution and dried over MgSO$_4$, and the solvent is evaporated under vacuum. The residue is chromatographed on silica gel, elution being carried out with a cyclohexane/EtOAc mixture from (80/20; v/v) to (40/60; v/v). 1.85 g of the expected compound are obtained.

Preparation 1.16

N-[3-(7-Nitro-1H-indol-1-yl)propyl]methanesulfonamide (II): $R_1$=—$NHSO_2CH_3$; $R_2$=H; $R_4$=H; $R_5$=7-$NO_2$ This compound is prepared according to processes described in stages B, C and D of Preparation 1.15 from 7-nitro-1H-indole.

Preparation 1.17

N-[3-(7-Fluoro-2-methyl-1H-indol-1-yl)propyl]trifluoromethanesulfonamide (II): $R_1$=—$NHSO_2CF_3$; $R_2$=$CH_3$; $R_4$=H; $R_5$=7-F A mixture of 4.14 g of 60% sodium hydride in oil in 200 ml of DMF is cooled to 5° C., a solution of 15.42 g of trifluoromethanesulfonamide in 150 ml of DMF is added and the mixture is left stirring at 5° C. for 5 minutes. A solution of 8.2 g of the compound from stage C of Preparation 1.5 in 100 ml of DMF is subsequently added and the mixture is left stirring overnight while allowing the temperature to return to AT. The reaction mixture is poured into water and extracted with DCM, the organic phase is washed with a saturated NaCl solution and dried over $MgSO_4$, and the solvent is evaporated under vacuum. The residue is chromatographed on silica gel, elution being carried out with cyclohexane and then with a cyclohexane/EtOAc mixture (80/20; v/v). 3.8 g of the expected compound are obtained.

EXAMPLE 1

Compound No. 1

N-[3-[3-(3,3-Dimethylbutanoyl)-2-methyl-1H-indol-1-yl]propyl]methanesulfonamide

A mixture of 0.95 g of the compound from Preparation 1.1 and 0.99 ml of 3,3-dimethylbutyryl chloride in 120 ml of DCM is cooled to −25° C. under a nitrogen atmosphere, 4 ml of a 1.8M solution of ethylaluminum dichloride in toluene are added and the mixture is left stirring for 5 hours while allowing the temperature to return to AT. The reaction mixture is poured into water and extracted with DCM, the organic phase is washed with a 10% HCl solution, with a 10% NaOH solution and with a saturated NaCl solution and dried over $MgSO_4$, and the solvent is evaporated under vacuum. The residue is chromatographed on silica gel, elution being carried out with DCM and then with the gradient of a DCM/MeOH mixture from (100/0.5; v/v) to (100/2; v/v). 0.22 g of the expected compound is obtained, M.p.=139-142° C.

EXAMPLE 2

Compound No. 13

N-[3-[3-[2-(2-Bromophenyl)-N-ethoxyethanimidoyl]-7-chloro-2-methyl-1H-indol-1-yl]propyl]methanesulfonamide A mixture of 0.38 g of compound No. 12, 0.75 g of O-ethylhydroxylamine hydrochloride and 3 ml of pyridine in 3.5 ml of ethanol is heated at reflux overnight. The reaction mixture is concentrated under vacuum, the residue is taken up in an ether/10% HCl mixture, the layers are separated by settling, the acidic aqueous phase is extracted with ether, the combined organic phases are washed with a saturated NaCl solution and dried over $MgSO_4$, and the solvent is evaporated under vacuum. The residue is chromatographed on silica gel, elution being carried out with DCM and then with the gradient of a DCM/MeOH mixture down to (97/3; v/v). 0.31 g of the expected compound is obtained.

EXAMPLE 3

Compound No. 53 and Compound No. 54

1-[7-Chloro-2-methyl-1-[3-(methylsulfinyl)propyl]-1H-indol-3-yl]-3,3-dimethylbutan-1-one and 1-[7-Chloro-2-methyl-1-[3-(methylsulfonyl)propyl]-1H-indol-3-yl]-3,3-dimethylbutan-1-one A mixture of 1.28 g of 3-chloroperbenzoic acid in 72 ml of DCM is cooled to 5° C., a solution of 1.31 g of compound No. 52 in 72 ml of DCM is added dropwise and the mixture is left stirring while allowing the temperature to return to AT. The reaction mixture is poured into a 10% NaOH solution and extracted with DCM, the organic phase is washed with water and then with 10% NaOH solution and dried over $MgSO_4$, and the solvent is evaporated under vacuum. The two compounds obtained are separated by preparative chromatography according to the following conditions:

Equipment: Delta Prep 4000 preparative HPLC system
 Waters Prep LC 4000 pump;
 Prochrom dynamic axial compression column: length: 300 mm; diameter 50 mm;
 TPS Spectra 100 single-wavelength detector;
Stationary phase: Kromasil C18 10 μm
 Compression pressure: 50 bar;
Mobile phase: eluent A: $H_2O$+0.1% TFA
 eluent B: acetonitrile/$H_2O$ (90/10; v/v)+0.1% TFA.
Gradient:

| t (minute) | % A | % B |
|---|---|---|
| 0 | 15 | 85 |
| 50 | 09 | 91 |
| 60 | 09 | 91 |

Flow rate: 124 ml/minute;
UV detection: λ=230 nm; cell length: 3.5 mm.
Conditions used for the HPLC analysis:
Equipment: Waters line with Millennium software;
Column: Uptisphere HDO 15 Q 55 μm; 150×4.6 mm;
Mobile phase: eluent A: $H_2O$+0.1% TFA
 eluent B: acetonitrile/$H_2O$ (90/10; v/v)+0.1% TFA
Gradient:

| t (minute) | % A | % B |
|---|---|---|
| 0 | 90 | 10 |
| 40 | 0 | 100 |
| 60 | 0 | 100 |

Flow rate: 1 ml/minute;
Wavelength: λ=230 nm.

After separation of the compounds, the following are obtained:
compound No. 53: w=0.257 g, M.p.=123° C., the reverse-phase purity of which is 99.8% (rt=31.13 min);
compound No. 54: w=0.358 g, M.p.=167° C., the reverse-phase purity of which is 98.3% (rt=34.95 min).

EXAMPLE 4

Compound No. 58

2-(2-Bromophenyl)-1-[6,7-dichloro-1-[3-(methylthio)propyl]indol-3-yl]ethanone oxime A mixture of 1.4 g of compound No. 57, 2.1 g of hydroxylamine hydrochloride and 12 ml of pyridine in 13 ml of ethanol is heated at 115° C. overnight. The reaction mixture is concentrated under vacuum, the residue is taken up in an ether/10% HCl mixture, the layers are separated by settling, the acidic aqueous phase is extracted with ether, the combined organic phases are washed with a saturated NaCl solution and dried over MgSO$_4$, and the solvent is evaporated under vacuum. 0.56 g of the expected compound is obtained after crystallization from ether, M.p.=139-142° C.

EXAMPLE 5

Compound No. 59

2-(2-Bromophenyl)-1-[6,7-dichloro-1-[3-(methylsulfonyl)propyl]-1H-indol-3-yl]ethanone oxime A mixture of 0.32 g of 3-chloroperbenzoic acid in 7 ml of DCM is cooled to 5° C., a solution of 0.25 g of compound No. 58 in 10 ml of DCM is added dropwise and the mixture is left stirring for 4 hours. The reaction mixture is poured into a 10% NaOH solution and extracted with DCM, the organic phase is washed with water and with a saturated NaCl solution and dried over MgSO$_4$, and the solvent is evaporated under vacuum. The residue is chromatographed on silica gel, elution being carried out with a cyclohexane/EtOAc mixture (50/50; v/v). 0.14 g of the expected compound is obtained, M.p.=191-194° C.

EXAMPLE 6

Compound No. 64 and Compound No. 65

2-(1-Adamantyl)-1-[6,7-dichloro-2-methyl-1-[3-(methylsulfinyl)propyl]-1H-indol-3-yl]ethanone and 2-(1-Adamantyl)-1-[6,7-dichloro-2-methyl-1-[3-(methylsulfonyl)propyl]-1H-indol-3-yl]ethanone These two compounds are prepared according to the procedure described in Example 3 from compound No. 63. The two compounds obtained are separated by preparative chromatography according to the same conditions as those described in Example 3. The Following are Obtained
compound No. 64: w=0.549 g, M.p.=116° C., the reverse-phase purity of which is 99.7% (rt=43.8 minutes),
compound No. 65: w=0.462 g, M.p.=174° C., the reverse-phase purity of which is 98.7% (rt=46.1 minutes).

The chemical structures and the physical properties of a few examples of compounds according to the invention are illustrated in the following table. In this table:

Me and Et respectively represent methyl and ethyl groups.

TABLE I (I)

[Structure of indole derivative with substituents X, R$_1$, R$_2$, R$_3$, R$_4$, R$_5$ on positions 4,5,6,7 of indole, with (CH$_2$)$_3$-R$_1$ on N and C(=X)-R$_3$ at position 3]

| Compound No. | X | R$_1$ | R$_2$ | R$_3$ | R$_4$ | R$_5$ | M.p.; NMR |
|---|---|---|---|---|---|---|---|
| 1 | O | NH—SO$_2$Me | Me | —CH$_2$—C(CH$_3$)$_3$ | H | H | 139-142 |
| 2 | O | NH—SO$_2$Me | Me | —CH$_2$—(2-chlorophenyl) 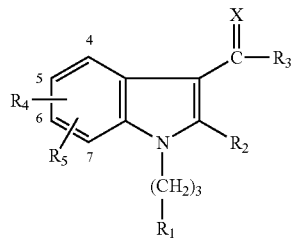 | H | H | 174-176 |

TABLE I-continued (I)

| Compound No. | X | R₁ | R₂ | R₃ | R₄ | R₅ | M.p.; NMR |
|---|---|---|---|---|---|---|---|
| 3 | O | NH—SO₂Me | Me | 1-methyl-1-phenylcyclopentyl | H | H | MH⁺ = 439 rt = 9.59 |
| 4 | O | NH—SO₂Me | Me | —C(CH₃)₃ | H | 7-Br | 89 |
| 5 | O | NH—SO₂Me | Me | —CH₂—C(CH₃)₃ | H | 7-Br | 93 |
| 6 | O | NH—SO₂Me | Me | —CH₂-(2-CF₃-phenyl) | H | 7-Br | 142 |
| 7 | O | NH—SO₂Me | Me | 1-(2-fluorophenyl)-1-methylcyclopentyl | H | 7-Br | 95 |
| 8 | O | NH—SO₂Me | Me | —CH₂—CH(CH₃)₂ | H | 7-Cl | 118-120 |
| 9 | O | NH—SO₂Me | Me | —CH₂—C(CH₃)₃ | H | 7-Cl | 113 |
| 10 | O | NH—SO₂Me | Me | —CH₂-adamantyl | H | 7-Cl | 55-60 |
| 11 | O | NH—SO₂Me | Me | —CH₂-phenyl | H | 7-Cl | 159-161 |
| 12 | O | NH—SO₂Me | Me | —CH₂-(2-Br-phenyl) | H | 7-Cl | 149-152 |
| 13 | =N—O-Et | NH—SO₂Me | Me | —CH₂-(2-Br-phenyl) | H | 7-Cl | MH⁺ = 540 rt = 10.58 |

TABLE I-continued (I)

[Structure: indole with positions 4,5,6,7; R4 at position 6 (with 5,6 and 7 labeled), R5 at position 7; N-(CH2)3-R1 on nitrogen; R2 at position 2; C(=X)-R3 at position 3]

| Compound No. | X | R₁ | R₂ | R₃ | R₄ | R₅ | M.p.; NMR |
|---|---|---|---|---|---|---|---|
| 14 | O | NH—SO₂Me | Me | —CH₂—(2-Cl-C₆H₄) | H | 7-Cl | 170-171 |
| 15 | =N—OH | NH—SO₂Me | Me | —CH₂—(2-Cl-C₆H₄) | H | 7-Cl | 57-60 |
| 16 | O | NH—SO₂Me | Me | —CH₂—(2-F-C₆H₄) | H | 7-Cl | 160-164 |
| 17 | O | NH—SO₂Me | Me | —CH₂—(3-OCH₃-C₆H₄) | H | 7-Cl | 119-122 |
| 18 | O | NH—SO₂Me | Me | —CH₂—(2-CF₃-C₆H₄) | H | 7-Cl | 139-141 NMR |
| 19 | O | NH—SO₂Me | Me | —CH₂—(3-CF₃-C₆H₄) | H | 7-Cl | 106-108 |
| 20 | O | NH—SO₂Me | Me | —CH₂—(4-CF₃-C₆H₄) | H | 7-Cl | 136-138 |
| 21 | O | NH—SO₂Me | Me | —CH₂—(2,4-Cl₂-C₆H₃) | H | 7-Cl | 141-144 |
| 22 | O | NH—SO₂Me | Me | —CH₂—(2,3-F₂-C₆H₃) | H | 7-Cl | 145-147 |

TABLE I-continued (I)

[Structure: indole with positions 4,5,6,7; R4 at 5/6, R5 at 7; N-(CH2)3-R1; C2-R2; C3-C(=X)-R3]

| Compound No. | X | R₁ | R₂ | R₃ | R₄ | R₅ | M.p.; NMR |
|---|---|---|---|---|---|---|---|
| 23 | O | NH—SO₂Me | Me | —CH₂—(2-F,3-CF₃-phenyl) | H | 7-Cl | 143-146 |
| 24 | O | NH—SO₂Me | Me | —CH₂—(3-CF₃,5-F-phenyl) | H | 7-Cl | 111-115 |
| 25 | O | NH—SO₂Me | Me | —CH₂—(4-CF₃,3-F-phenyl) | H | 7-Cl | 120-124 |
| 26 | O | NH—SO₂Me | Me | —CH₂—(1-naphthyl) | H | 7-Cl | 128-130 |
| 27 | O | NH—SO₂Me | Me | —CH₂—(2-naphthyl) | H | 7-Cl | 163-165 |
| 28 | O | NH—SO₂Me | Me | —CH₂CH₂—phenyl | H | 7-Cl | 137-140 |
| 29 | O | NH—SO₂Me | Me | —CH₂CH₂—(2-Cl-phenyl) | H | 7-Cl | 127-129 |
| 30 | =N—OH | NH—SO₂Me | Me | —CH₂CH₂—(2-Cl-phenyl) | H | 7-Cl | 58-60 |

TABLE I-continued
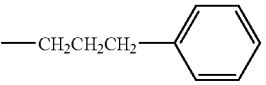
(I)
| Compound No. | X | $R_1$ | $R_2$ | $R_3$ | $R_4$ | $R_5$ | M.p.; NMR |
|---|---|---|---|---|---|---|---|
| 31 | O | NH—SO$_2$Me | Me | —CH$_2$CH$_2$CH$_2$—phenyl | H | 7-Cl | 127-130 |
| 32 | O | NH—SO$_2$Me | Me | 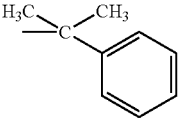 | H | 7-Cl | MH$^+$ = 447 rt = 9.61 |
| 33 | O | NH—SO$_2$Me | Me | 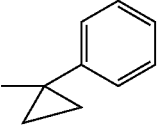 | H | 7-Cl | 107-110 |
| 34 | O | NH—SO$_2$Me | Me | 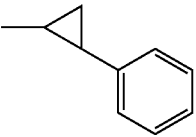 | H | 7-Cl | 179-180 |
| 35 | O | NH—SO$_2$Me | Me | 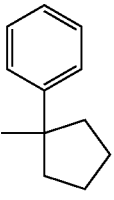 | H | 7-Cl | MH$^+$ = 473 rt = 10.30 |
| 36 | =N—O—Me | NH—SO$_2$Me | Me | 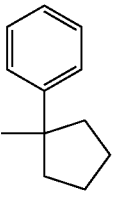 | H | 7-Cl | 68-71 |
| 37 | O | NH—SO$_2$Me | Me | 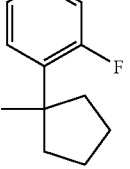 | H | 7-Cl | 103 |

TABLE I-continued (I)

| Compound No. | X | $R_1$ | $R_2$ | $R_3$ | $R_4$ | $R_5$ | M.p.; NMR |
|---|---|---|---|---|---|---|---|
| 38 | O | NH—SO$_2$Me | Me | 1-methyl-1-phenylcyclohexyl | H | 7-Cl | 59-62 |
| 39 | O | NH—SO$_2$Me | Me | —CH$_2$—CH(Ph)$_2$ | H | 7-Cl | 129-132 |
| 40 | O | NH—SO$_2$Me | Et | —CH$_2$—(2-CF$_3$-C$_6$H$_4$) | H | 7-Cl | 107-109 |
| 41 | O | NH—SO$_2$Me | Me | —CH$_2$—(2-CF$_3$-C$_6$H$_4$) | H | 7-F | 112-115 |
| 42 | O | NH—SO$_2$Me | Me | —CH$_2$—C(CH$_3$)$_3$ | 6-CH$_3$ | 7-Br | 110-114 |
| 43 | O | NH—SO$_2$Me | Me | —CH$_2$—(2-Cl-C$_6$H$_4$) | 6-CH$_3$ | 7-Br | 179-181 |
| 44 | O | NH—SO$_2$Me | H | —CH$_2$—(2-CF$_3$-C$_6$H$_4$) | 6-Cl | 7-Cl | 182-186 |
| 45 | O | NH—SO$_2$Me | Me | —CH$_2$—C(CH$_3$)$_3$ | 6-Cl | 7-Cl | 119-122 |
| 46 | O | NH—SO$_2$Me | Me | —CH$_2$—(2-CF$_3$-C$_6$H$_4$) | 6-Cl | 7-Cl | 157-159 |

TABLE I-continued
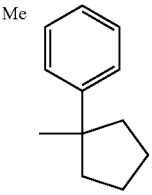
(I)
| Compound No. | X | R₁ | R₂ | R₃ | R₄ | R₅ | M.p.; NMR |
|---|---|---|---|---|---|---|---|
| 47 | O | NH—SO₂Me | Me | 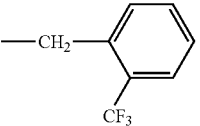 | 6-Cl | 7-Cl | MH⁺ = 507<br>rt = 10.95 |
| 48 | O | NH—SO₂Me | Me | 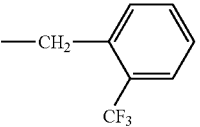 | 6-Cl | 7-Cl | 159-162 |
| 49 | O | NH—SO₂—CF₃ | Me | 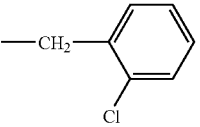 | H | 7-Cl | 127-130 |
| 50 | O | NHSO₂N(Me)₂ | Me | 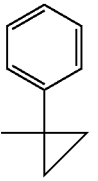 | 6-Cl | 7-Cl | 181 |
| 51 | O | NHSO₂N(Me)₂ | Me | 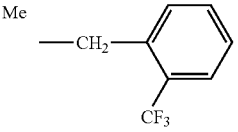 | 6-Cl | 7-Cl | MH⁺ = 508<br>rt = 10.26 |
| 52 | O | —S—Me | Me | —CH₂—C(CH₃)₃ | H | 7-Cl | MH⁺ = 352<br>rt = 11.75 |
| 53 | O | —SO—Me | Me | —CH₂—C(CH₃)₃ | H | 7-Cl | 123 |
| 54 | O | —SO₂—Me | Me | —CH₂—C(CH₃)₃ | H | 7-Cl | 167 |
| 55 | O | —S—Me | Me | 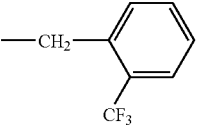 | H | 7-Cl | 76-80 |
| 56 | O | —SO₂—Me | Me | —CH₂-(2-CF₃-C₆H₄) | H | 7-Cl | 140-142 |

TABLE I-continued (I)

| Compound No. | X | R₁ | R₂ | R₃ | R₄ | R₅ | M.p.; NMR |
|---|---|---|---|---|---|---|---|
| 57 | O | —S—Me | H | —CH₂—(2-Br-phenyl) | 6-Cl | 7-Cl | 138-140 |
| 58 | =N—OH | —S—Me | H | —CH₂—(2-Br-phenyl) | 6-Cl | 7-Cl | 139-142 |
| 59 | =N—OH | —SO₂—Me | H | —CH₂—(2-Br-phenyl) | 6-Cl | 7-Cl | 191-194 |
| 60 | =N—O—Me | —S—Me | H | —CH₂—(2-Br-phenyl) | 6-Cl | 7-Cl | 76-77 |
| 61 | =N—O—Me | —SO₂—Me | H | —CH₂—(2-Br-phenyl) | 6-Cl | 7-Cl | 141-144 |
| 62 | O | —SO₂—Me | H | —CH₂—(2-Br-phenyl) | 6-Cl | 7-Cl | 184 |
| 63 | O | —S—Me | Me | —CH₂—adamantyl | 6-Cl | 7-Cl | 108 |
| 64 | O | —SO—Me | Me | —CH₂—adamantyl | 6-Cl | 7-Cl | 116 |
| 65 | O | —SO₂—Me | Me | —CH₂—adamantyl | 6-Cl | 7-Cl | 174 |

TABLE I-continued
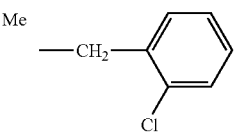
(I)
| Compound No. | X | R₁ | R₂ | R₃ | R₄ | R₅ | M.p.; NMR |
|---|---|---|---|---|---|---|---|
| 66 | O | —NH—SO₂—Me | Me | 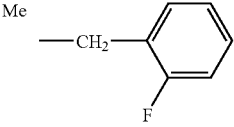 —CH₂—C₆H₄—Cl (2-Cl) | H | 7-Br | 178-180 |
| 67 | O | —NH—SO₂—Me | Me | 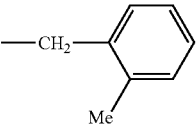 —CH₂—C₆H₄—F (2-F) | H | 7-Br | 168-169 |
| 68 | O | —NH—SO₂—Me | Me | 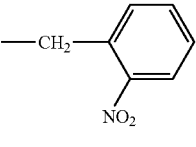 —CH₂—C₆H₄—Me (2-Me) | H | 7-Br | 184-186 |
| 69 | O | —NH—SO₂—Me | Me | —CH₂—C₆H₄—NO₂ (2-NO₂) | H | 7-Br | 181 |
| 70 | O | —NH—SO₂—Me | Me | 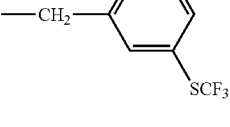 —CH₂—C₆H₄—SCF₃ (3-SCF₃) | H | 7-Br | 118-119 |
| 71 | O | —NH—SO₂—Me | Me | 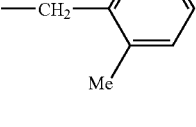 —CH₂—C₆H₄—Me (2-Me) | H | 7-Cl | 178-180 |
| 72 | O | —NH—SO₂—Me | Me | 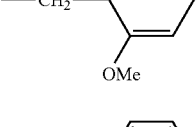 —CH₂—C₆H₄—OMe (2-OMe) | H | 7-Cl | 126-128 |
| 73 | O | —NH—SO₂—Me | Me | 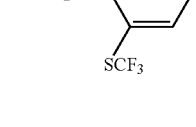 —CH₂—C₆H₄—SCF₃ (2-SCF₃) | H | 7-Cl | 142-144 |

TABLE I-continued (I)

Structure: indole with positions 4,5,6,7 labeled; R4 at 6, R5 at 7; N-(CH2)3-R1; 2-position R2; 3-position C(=X)-R3.

| Compound No. | X | R₁ | R₂ | R₃ | R₄ | R₅ | M.p.; NMR |
|---|---|---|---|---|---|---|---|
| 74 | O | —NH—SO₂—Me | Me | —CH₂-(2-Br-phenyl) | H | 7-F | 155-157 |
| 75 | O | —NH—SO₂—Me | Me | —CH₂-(2-Cl-phenyl) | H | 7-F | 143-146 |
| 76 | O | —NH—SO₂—Me | Me | —CH₂-(2-F-phenyl) | H | 7-F | 145-147 |
| 77 | O | —NH—SO₂—Me | Me | —CH₂-(2-Me-phenyl) | H | 7-F | 56-58 |
| 78 | O | —NH—SO₂—Me | Me | —CH₂-(2-OMe-phenyl) | H | 7-F | 113-116 |
| 79 | O | —NH—SO₂—Me | Me | —CH₂-(2-CF₃-phenyl) | 6-Me | 7-Br | 149-152 |
| 80 | O | —NH—SO₂—Me | Me | —CH₂-(2-Br-phenyl) | H | 7-OMe | 164-167 |
| 81 | O | —NH—SO₂—Me | Me | —CH₂-(2-CF₃-phenyl) | H | 7-OMe | 182-184 |

TABLE I-continued
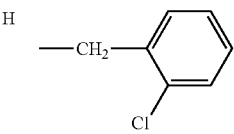
(I)
| Compound No. | X | R₁ | R₂ | R₃ | R₄ | R₅ | M.p.; NMR |
|---|---|---|---|---|---|---|---|
| 82 | O | —NH—SO₂—Me | H | —CH₂—C₆H₄—Cl (2-Cl) | H | 7-NO₂ | 177-178 |
| 83 | O | —NH—SO₂—Me | H | —CH₂—C₆H₄—F (2-F) | H | 7-NO₂ | 177-178 |
| 84 | O | —NH—SO₂—Me | H | —CH₂—C₆H₄—Me (2-Me) | H | 7-NO₂ | 135-137 |
| 85 | O | —NH—SO₂—Me | H | —CH₂—C₆H₄—CF₃ (2-CF₃) | H | 7-NO₂ | 162-165 |
| 86 | O | —NH—SO₂—Me | H | —CH₂—C₆H₄—Br (2-Br) | H | 7-NO₂ | 184-187 |
| 87 | O | —NH—SO₂—Me | H | —CH₂—C₆H₄—OMe (2-OMe) | H | 7-NO₂ | 178-179 |
| 88 | O | —NH—SO₂—Me | H | —CH₂—C₆H₄—OCF₃ (2-OCF₃) | H | 7-NO₂ | 168-170 |
| 89 | O | —NH—SO₂—Me | H | —CH₂—C₆H₄—NO₂ (2-NO₂) | H | 7-NO₂ | 156-159 |

TABLE I-continued (I)

| Compound No. | X | R₁ | R₂ | R₃ | R₄ | R₅ | M.p.; NMR |
|---|---|---|---|---|---|---|---|
| 90 | O | —NH—SO₂—Me | Me | —CH₂—C₆H₄(2-Br) | H | 7-Br | 187-189 |
| 91 | O | —NH—SO₂—Me | Me | —CH₂—C₆H₄(2-OMe) | H | 7-Br | 67-70 |
| 92 | O | —NH—SO₂—Me | Me | —CH₂—C₆H₄(2-OCF₃) | H | 7-Br | 156-159 |
| 93 | O | —NH—SO₂—Me | Me | —CH₂—C₆H₄(2-OCF₃) | H | 7-F | 119-122 |
| 94 | O | —NH—SO₂—Me | Me | —CH₂—C₆H₄(2-NO₂) | H | 7-F | 65-67 |
| 95 | O | —NH—SO₂—CF₃ | Me | —CH₂—C₆H₄(2-Br) | H | 7-Cl | 139-141 |
| 96 | O | —NH—SO₂—CF₃ | Me | —CH₂—C₆H₄(2-Cl) | H | 7-Cl | 135-138 |
| 97 | O | —NH—SO₂—CF₃ | Me | —CH₂—C₆H₄(2-F) | H | 7-Cl | 141-144 |

TABLE I-continued

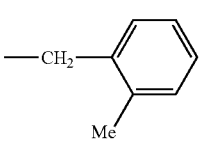

| Compound No. | X | R₁ | R₂ | R₃ | R₄ | R₅ | M.p.; NMR |
|---|---|---|---|---|---|---|---|
| 98 | O | —NH—SO₂—CF₃ | Me | —CH₂—C₆H₄—Me (o) | H | 7-Cl | 135-137 |
| 99 | O | —NH—SO₂—CF₃ | Me | —CH₂—C₆H₄—OMe (o) | H | 7-Cl | 178-180 |
| 100 | O | —NH—SO₂—CF₃ | Me | —CH₂—C₆H₄—Br (o) | H | 7-F | 63-65 |
| 101 | O | —NH—SO₂—CF₃ | Me | —CH₂—C₆H₄—OMe (o) | H | 7-F | 152-155 |
| 102 | O | —NH—SO₂—CF₃ | Me | —CH₂—C₆H₄—CF₃ (o) | H | 7-F | 151-154 |
| 103 | O | —NH—SO₂—Me | Me | —CH₂—C₆H₄—CN (o) | H | 7-Br | 211-213 |

Compound No. 18: $^1$H NMR: d$_6$-DMSO: δ (ppm): 1.95: mt: 2H, 2.75: s: 3H, 2.95: s: 3H, 3.15: q: 2H, 4.4-4.8: s+mt: 4H, 7.15-7.4: mt: 3H, 7.5: mt: 2H, 7.6-7.8: mt: 2H, 8.1: d: 1H.

The compounds according to the invention have shown a good in vitro affinity for (CB$_2$) cannabinoid receptors and a markedly lower in vitro affinity for (CB$_1$) cannabinoid receptors, whether human receptors or rodent receptors. Affinity binding tests were carried out according to the experimental conditions described by M. Rinaldi-Carmona in J. Pharmacol. Exp. Therap., 1998, 287, 644-650, with membranes resulting from rodent tissues and from cell lines in which CB$_1$ receptors (Matsuda et al., Nature 1990, 346, 561-564) and CB$_2$ receptors (Munro et al., Nature 1993, 365, 61-65) were expressed.

The in vitro affinity for cannabinoid receptors is expressed in the form of IC$_{50}$ (concentration causing 50% inhibition of the specific binding of the control).

For human receptors, the in vitro affinity to CB$_2$ cannabinoids, expressed in the form of IC$_{50}$, is less than 500 nM.

The agonist nature of the compounds according to the invention was demonstrated by the results obtained in the models of the inhibition of adenylate cyclase as described in M. Rinaldi-Carmona et al., J. Pharmacol. Exp. Ther., 1996, 278, 871-878 and 1998, 284, 644-650 and M. Bouaboula et al., J. Biol. Chem., 1997, 272, 22330-122339.

The compounds of the present invention are in particular active principles for pharmaceutical compositions, the toxicity of which is compatible with their use as medicaments.

According to one of its aspects, the present invention relates to the use of a compound of formula (I) or of one of its pharmaceutically acceptable salts or solvates in the preparation of medicaments intended to prevent or to treat any human pathology and/or for veterinary use in which $CB_2$ cannabinoid receptors are implicated.

Mention may be made, for example, of the following diseases or conditions:

disorders of the immune system, in particular autoimmune diseases: psoriasis, lupus erythematosus, diseases of the connective tissue, Sjögren's syndrome, ankylosing spondylarthritis, rheumatoid arthritis, rectional arthritis, undifferentiated spondylarthritis, Behcet's disease, autoimmune hemolytic anemias, multiple sclerosis, amyotrophic lateral sclerosis, amyloidosis, graft rejection or diseases affecting the plasma cell line; allergic diseases: delayed or immediate hypersensitivity, allergic rhinitis, contact dermatitis or allergic conjunctivitis; infectious parasitic, viral or bacterial diseases: AIDS or meningitis; amyloidosis, diseases affecting the lines of the lymphohaematopoietic system; chronic liver diseases of alcoholic, viral and toxic origin, and also steatohepatitis of nonalcoholic origin and primary liver cancer; inflammatory diseases, in particular diseases of the joints: arthritis, rheumatoid arthritis, osteoarthritis, spondylitis, gout, vasculitis, Crohn's disease, inflammatory bowel disease (IBD) or irritable bowel syndrome (IBS), or pancreatitis; osteoporosis; pain: chronic pain of inflammatory type, neuropathic pain or acute peripheral pain; eye conditions: ocular hypertension or glaucoma; pulmonary conditions: diseases of the respiratory tract, asthma, chronic bronchitis, chronic obstructive pulmonary disease (COPD) or emphysema; diseases of the central nervous system and neurodegenerative diseases: Tourette's syndrome, Parkinson's disease, Alzheimer's disease, senile dementia, chorea, Huntington's chorea, epilepsy, psychoses, depression or spinal cord lesions; migraine, dizziness, vomiting or nausea, in particular that resulting from a chemotherapy; cardiovascular diseases, in particular hypertension, arteriosclerosis, heart attack or cardiac ischaemia; renal ischaemia; cancers: benign skin tumors, cancerous tumors and papillomas, prostate tumors or brain tumors (glioblastomas, medulloepitheliomas, medulloblastomas, neuroblastomas, tumors of embryonic origin, astrocytomas, astroblastomas, ependymomas, oligodendrogliomas, plexus tumors, neuroepitheliomas, tumor of the epiphysis, ependymoblastomas, neuroectodermal tumor, malignant meningiomas, sarcomatoses, malignant melanomas or schwannomas); gastrointestinal diseases; obesity; or diabetes.

The use of the compounds according to the invention for the prevention and/or treatment of the abovementioned diseases and in the preparation of medicaments intended to treat these diseases forms an integral part of the invention.

The compounds of formula (I) above, or one of their pharmaceutically acceptable salts or solvates, can be used at daily doses of 0.01 to 100 mg per kilo of body weight of the mammal to be treated, preferably at daily doses of 0.1 to 50 mg/kg. In man, the dose can preferably vary from 0.1 to 4000 mg per day, more particularly from 0.5 to 1000 mg, depending on the age of the subject to be treated or the type of treatment, prophylactic or curative.

Thus, according to another of its aspects, the present invention relates to pharmaceutical compositions including, as active principle, a compound of formula (I) or one of its pharmaceutically acceptable salts or solvates and also one or more pharmaceutically acceptable excipients.

In the pharmaceutical compositions of the present invention for oral, sublingual, inhaled, subcutaneous, intramuscular, intravenous, topical, local, intratracheal, intranasal, transdermal or rectal administration, the active principles can be administered in unit administration forms, as a mixture with conventional pharmaceutical vehicles, to animals and to human beings.

The appropriate unit administration forms comprise oral forms, such as tablets, soft or hard gelatin capsules, powders, granules, oral solutions or suspensions, sublingual, buccal, intratracheal, intraocular, intranasal or inhalatory administration forms, aerosols, topical or transdermal administration forms, implants, subcutaneous, intramuscular or intravenous administration forms and rectal administration forms.

For topical administration, the compounds according to the invention can be used in creams, ointments, gels or lotions.

By way of example, a unit administration form of a compound according to the invention in a tablet form can comprise the following components:

| | |
|---|---|
| Compound according to the invention: | 50.0 mg |
| Mannitol: | 223.75 mg |
| Sodium croscarmellose: | 6.0 mg |
| Maize starch: | 15.0 mg |
| Hydroxypropylmethylcellulose: | 2.25 mg |
| Magnesium stearate: | 3.0 mg |

Orally, the dose of active principle administered per day can reach 0.01 to 100 mg/kg, taken once or several times, preferably 0.02 to 50 mg/kg.

There may be particular cases where higher or lower dosages are appropriate; such dosages do not depart from the scope of the invention. According to the normal practice, the dosage appropriate to each patient is determined by the physician according to the method of administration and the weight and the response of the said patient.

According to another of its aspects, the present invention also relates to a method for the treatment of the pathologies indicated above which comprises the administration, to a patient, of an effective dose of a compound according to the invention, or hydrates or solvates.

The compounds according to the invention can also be used in the preparation of compositions for veterinary use.

Furthermore, the compounds according to the invention, as is or in the radiolabeled form, can be used as pharmacological tools in man or in animals for the detection and the labeling of $CB_2$ cannabinoid receptors.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

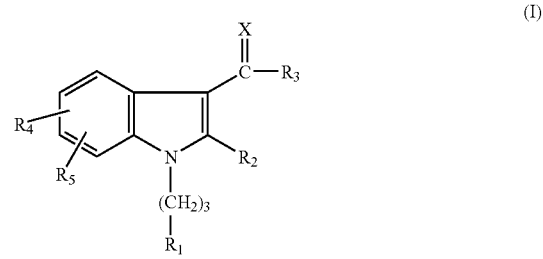

wherein:

X represents an oxygen atom;

$R_1$ represents a $-N(R_7)SO_2R_8$;

$R_2$ represents a hydrogen atom or a $(C_1-C_4)$alkyl;

$R_3$ represents:

a $(C_1-C_6)$alkyl which is unsubstituted or substituted by:
  a naphthyl which is unsubstituted or substituted one or more times by substituents chosen independently from a halogen atom, a $(C_1-C_4)$alkyl, a $(C_1-C_4)$alkoxy or a trifluoromethyl radical;

$R_4$ and $R_5$ each independently represent a hydrogen atom, a halogen atom, a $(C_1-C_4)$alkyl, a $(C_1-C_4)$alkoxy, a trifluoromethyl radical or a nitro;

$R_7$ represents a hydrogen atom or a $(C_1-C_4)$alkyl; and $R_8$ represents a $(C_1-C_4)$alkyl or a trifluoromethyl radical; or a salt thereof.

2. The compound of formula (I) according to claim 1, wherein:

X represents an oxygen atom;

$R_1$ represents a group chosen from $-NHSO_2CH_3$, or $-NHSO_2CF_3$;

$R_2$ represents a hydrogen atom, a methyl or an ethyl;

$R_3$ represents:
  a tert-butyl, an isobutyl, a 2,2-dimethylpropyl, or a naphthylmethyl, $R_4$ represents a hydrogen atom or is in the 6-position of the indole and represents a chlorine atom or a methyl; and $R_5$ represents a hydrogen atom or is in the 7-position of the indole and represents a bromine, chlorine or fluorine atom, a methoxy or a nitro.

3. The compound of formula (I) according to claim 1, wherein:

X represents an oxygen atom;

$R_1$ represents a group chosen from $-NHSO_2CH_3$, or $-NHSO_2CF_3$;

$R_2$ represents a methyl or an ethyl;

$R_4$ represents a hydrogen atom or is in the 6-position of the indole and represents a chlorine atom or a methyl; and $R_5$ represents a hydrogen or is in the 7-position of the indole and represents a bromine, chlorine or fluorine atom, a methoxy or a nitro.

4. The compound of formula (I) according to claim 1, wherein:

X represents an oxygen atom;

$R_1$ represents a group chosen from $-NHSO_2CH_3$, or $-NHSO_2CF_3$;

$R_2$ represents a methyl;

$R_4$ represents a hydrogen atom or is in the 6-position of the indole and represents a chlorine atom or a methyl; and $R_5$ represents a hydrogen or is in the 7-position of the indole and represents a bromine, chlorine or fluorine atom, a methoxy or a nitro.

5. The compound of formula (I) according to claim 1 chosen from:
  —N-[3-[7-bromo-3-(3,3-dimethylbutanoyl)-2-methyl-1H-indol-1-yl]propyl]methanesulfonamide;
  —N-[3-[7-chloro-3-(3,3-dimethylbutanoyl)-2-methyl-1H-indol-1-yl]propyl]methanesulfonamide; and
  —N-[3-[7-bromo-3-(3,3-dimethylbutanoyl)-2,6-dimethyl-1H-indol-1-yl]propyl]methanesulfonamide;
or a salt thereof.

6. A process for the preparation of a compound of formula (I) according to claim 1 in which X represents an oxygen atom, comprising:

reacting a compound of formula (II):

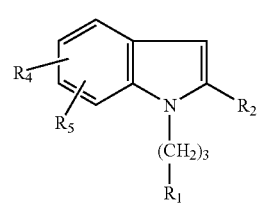

(II)

in which $R_1$, $R_2$, $R_4$ and $R_5$ are as defined in claim 1, in the presence of a Lewis acid, with an acid halide of formula (III):

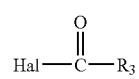

(III)

in which $R_3$ is as defined in claim 1 and Hal represents a halogen atom.

7. A pharmaceutical composition comprising a compound of formula (I) according to claim 1 or a pharmaceutically acceptable salt thereof in combination with at least one pharmaceutically acceptable excipient.

8. A pharmaceutical composition comprising a compound of formula (I) according to claim 2 or a pharmaceutically acceptable salt thereof in combination with at least one pharmaceutically acceptable excipient.

9. A pharmaceutical composition comprising a compound of formula (I) according to claim 3 or a pharmaceutically acceptable salt thereof in combination with at least one pharmaceutically acceptable excipient.

10. A pharmaceutical composition comprising a compound of formula (I) according to claim 4 or a pharmaceutically acceptable salt thereof in combination with at least one pharmaceutically acceptable excipient.

11. A pharmaceutical composition comprising a compound of formula (I) according to claim 5 or a pharmaceutically acceptable salt thereof in combination with at least one pharmaceutically acceptable excipient.

* * * * *